United States Patent [19]
Karell

[11] Patent Number: 6,006,746
[45] Date of Patent: Dec. 28, 1999

[54] NASAL DILATOR IN COMBINATION WITH EYEGLASS

[76] Inventor: Manuel L. Karell, 3573 - 22 St., San Francisco, Calif. 94114

[21] Appl. No.: 09/087,204

[22] Filed: May 30, 1998

[51] Int. Cl.⁶ .................................................. A61M 15/00
[52] U.S. Cl. ............................... 128/200.24; 128/207.18; 128/848; 606/199; 606/204.45
[58] Field of Search .......... 128/200.24, 207.18, 128/848, 912, DIG. 26; 606/199, 204.45; 351/136

[56] References Cited

U.S. PATENT DOCUMENTS

| | | | |
|---|---|---|---|
| 2,965,099 | 4/1960 | Aufricht | 606/199 |
| 5,533,503 | 7/1996 | Doubek . | |
| 5,653,224 | 8/1997 | Johnson | 128/200.24 |
| 5,718,224 | 2/1998 | Muchin | 128/200.24 |
| 5,842,469 | 12/1998 | Rapp et al. | 128/200.24 |

*Primary Examiner*—Aaron J. Lewis
*Assistant Examiner*—Teena Mitchell

[57] ABSTRACT

An eyeglass frame structure having combined a pair of nasal dilators for the relief of nasal passageway airflow. Each dilator means comprises a spring member which is substantially curved to follow the lens receiving portion of the frame and which is adapted to engage the eyeglass frame. The distal portion of the spring member comprises an adhesive for releasably securing to a user's nose. The potential energy force of the dilator adhered to the nose prevents outer wall tissue of nasal passages of a nose from drawing in during breathing. The nasal dilator may or may not be in unity with the eyeglass frame structure.

22 Claims, 5 Drawing Sheets

NASAL DILATOR IN COMBINATION WITH EYEGLASS

BACKGROUND OF THE INVENTION

This invention relates generally to the field of nasal dilators for preventing outer wall tissue of nasal passages of a nose from drawing in during breathing. In particular, the present invention is for use in combination with eyeglasses.

Many individuals have some malformation of the nasal passages which makes breathing difficult. Nasal obstructions commonly occur in individuals who have swelling due to allergic reactions, colds, a deviated septum or similar condition, to the point that the nasal airway may be substantially blocked. Blocked nasal passages causes mouth breathing which may be deleterious to health.

An approach to nasal blockage are nasal dilators, such as U.S. Pat. No. 5,533,503 to Doubek, 1994, which teaches a truss member including a resilient flexible strip of material acting to stabilize the outer wall tissue and thereby prevents the nasal passages from drawing in during breathing. The nasal dilator is adhered to the skin of the nose. Many eyeglass wearers find that the nasal dilator interferes with eyeglass positioning on the nose, and thus become incompatible. Also, the nasal dilator is cosmetically obtrusive. The nasal dilator may itself be uncomfortable to wear. The present invention overrides such problems.

SUMMARY OF THE INVENTION

The present invention is a combination eyeglass and nasal dilator. The eyeglass frame has at least one nasal dilator permanently or not permanently attached to the frame structure. The nasal dilator is generally located between the glass receptacles and a user's nose and its free end dilator comprises a resilient band or spring member having an adhesive tip for securing to the nose. The resiliency of the band or spring member attached to the eyeglass frame has a potential energy force which tends to move towards the frame and away from the nose. The adhesive allows for a releasably secured nasal dilator to the nose. The resilient dilator with its attending potential energy, now attached to the nose, wishes to move towards the frame, and as it does, it pulls with it nasal passageway tissue, thereby opening the vestibule of the nose, thereby increasing the ability to breathe. The dilator prevents nasal tissue from being drawn inwards during breathing.

The nasal dilator eyeglass combination can be comfortably and reliably worn through extended periods and assists is stabilizing eyeglass to the nose. This action adds comfort and security that eyeglasses will stay in position during daytime, while at the same time improving ability to breathe. The nasal dilator may comprises clear, nearly invisible material to improve cosmetic appearance.

An alternative embodiment is for the nasal dilator not in unity with the eyeglass frame structure, but to be used in conjunction with eyeglasses. In this embodiment, the nasal dilator is attachable to the eyeglass frame. The attaching means may be mechanical or adhesive, permanent or not permanent. For example, the nasal dilator may be clipped onto the eyeglass frame and then releasably adhesively secured to the nose. Or the nasal dilator may be permanently attachable to the eyeglass frame. Also a nasal dilator may be configured to have double sided adhesive capable of releasably securing to eyeglass frame while at the same time releasably securing to a nose. In this embodiment, the nasal dilator may be disposable.

The instant invention may be a nasal dilator comprising a truss member. The truss may be of breathable material, composed of one or more layers. The truss member may include a flexible strip of material having a first end region, a second end region and an intermediate segment. The first end region is adapted to engage an eyeglass frame. The adapting means may be mechanical or adhesive. The second end region is adapted to engage the outer wall tissue of nasal passages of the nose. The intermediate segment is configured to generally follow the curve of the lens receiving means of the eyeglass frame. The truss member further includes one or more resilient band means secured to the truss adjacent opposite edges of the intermediate segment. The resiliency of the resilient band acts to stabilize the outer wall tissue and thereby prevents the outer wall tissue of the nasal passages from drawing in during breathing. An adhesive means may be directly applied to the truss or to the resilient band means.

DETAILED DESCRIPTION OF THE PREFERRED EMBODIMENTS

Figure 1:
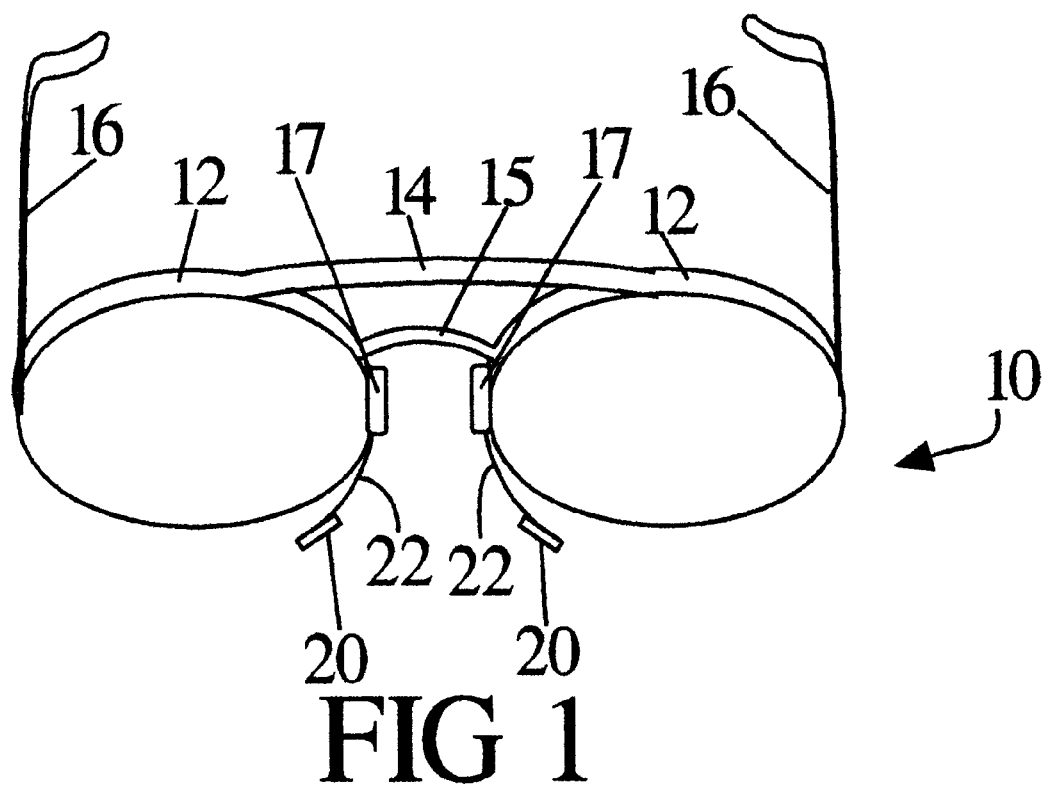
FIG. 1 is shows a pair of permanent nasal dilators mounted onto an eyeglass frame structure comprising resilient band members with adhesive means.
Figure 2:
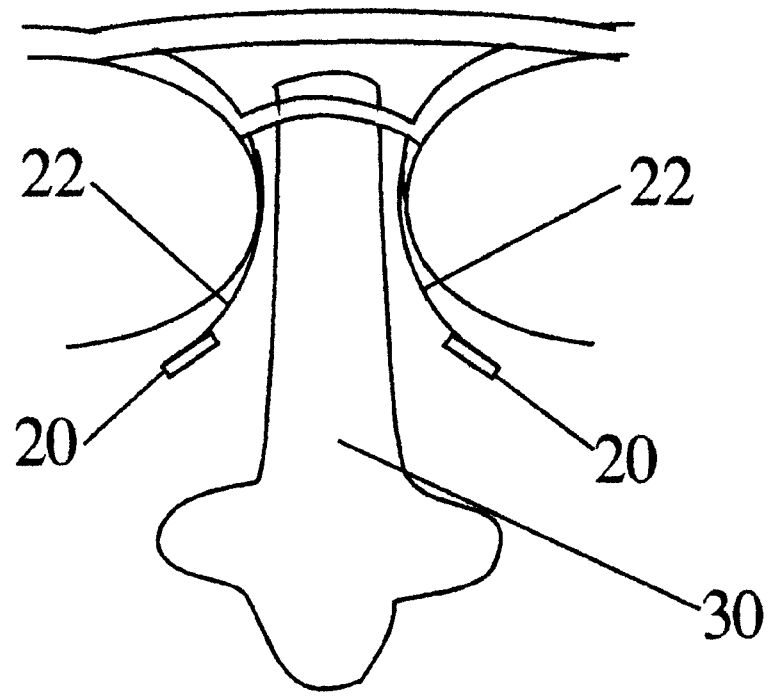
FIG. 2 is a close-up view showing the resilient band members and adhesive means in relation to a nose, with the nasal dilators in the resting position capable of having potential force wishing to move towards the frame and away from nose.
Figure 3:
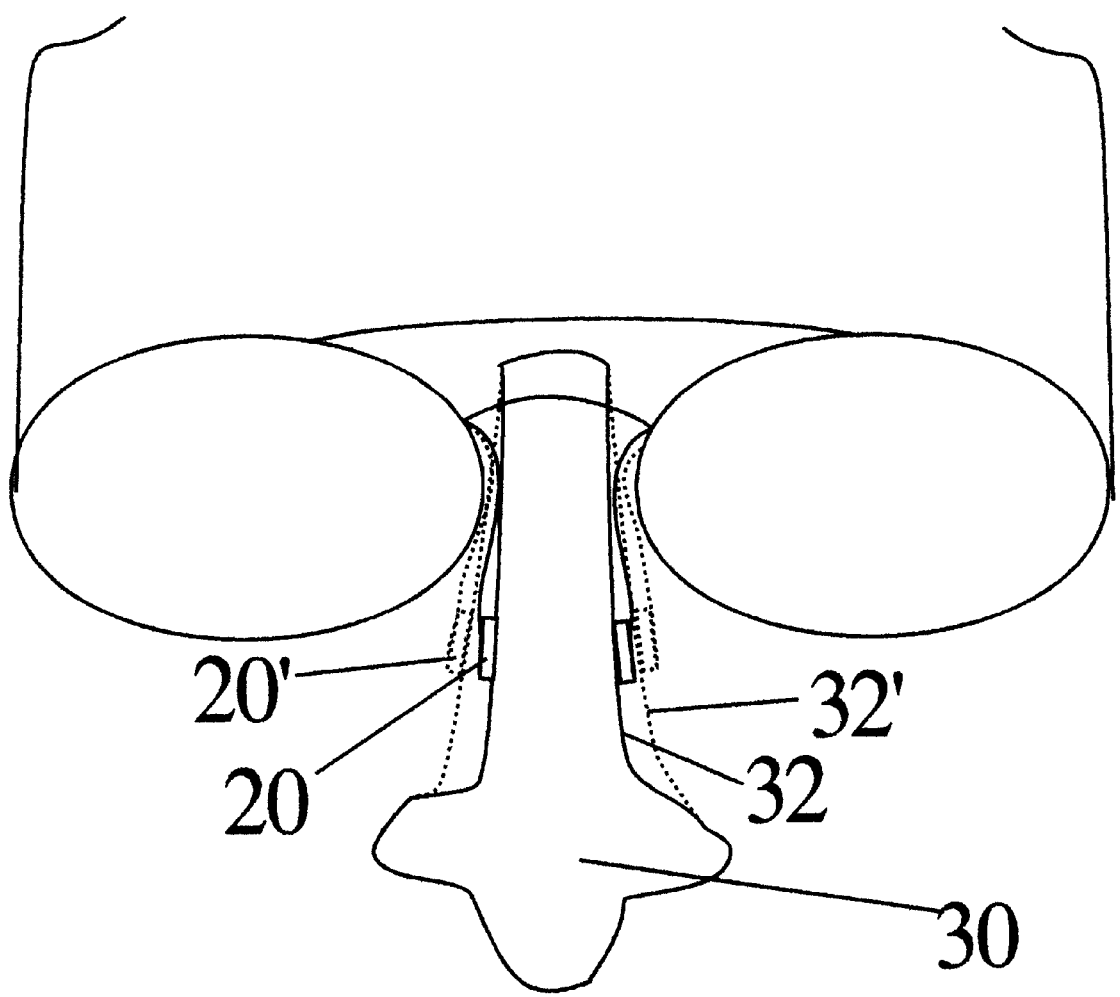
FIG. 3 is a greatly enlarged schematic view illustrating the adhesive means secured to the nose and providing a pulling force away from nose and towards the eyeglass frame, thereby opening nasal tissue passageway and preventing tissue from drawing in during breathing.

A eyeglass frame structure(10) in combination with nasal dilators of the present invention is generally illustrated in FIG. 1. Device(10) comprises an eyeglass frame structure having a frame member comprising a pair of lens receiving means(12), a first frame support bridge(14), a second frame support bridge(15), a pair of nasal pads(17), a pair of temple members(16) hingedly mounted to said frame member, and a pair of nasal dilators(22). Each nasal dilator comprises a resilient band member(22) having a nasal side and a frame side, with an adhesive means(20) mounted on the nasal side. FIG. 2 shows the resilient band member(22) with a potential force tending to pull towards the eyeglass frame member. FIG. 3 shows an adhesive means(20) secured to a nose(32). The potential force within the resilient band member tends to pull towards the eyeglass frame member. When the resilient band member is attached to the nose, the resilient potential force (i.e., the tendency of the resilient band member to return to their normally curved state shown in FIG. 2) now provides a pulling traction represented by dotted lines(32'), as nasal dilator means comes to rest in position(20'), thereby providing an opening force to nasal passage for increased air flow. The user places device(10) onto his/her face, places the temple members(16) on either side of face near ears, and rests nasal pads(17) onto nose. He/she then presses the nasal dilator means onto nose wherein it becomes adhered to nose by adhesive means(20). The eyeglass with nasal dilator combination is now in place. The resilient band member(22) exerts a force outwardly pulling the nose, represented by dotted lines(32'), thereby preventing outer wall tissue of nasal passages of a nose from drawing in during breathing.

The resilient band members may be attached to any portion of eyeglass frame structure, for example, the support bridges, nose pads, or lens receiving means.

Figure 5:
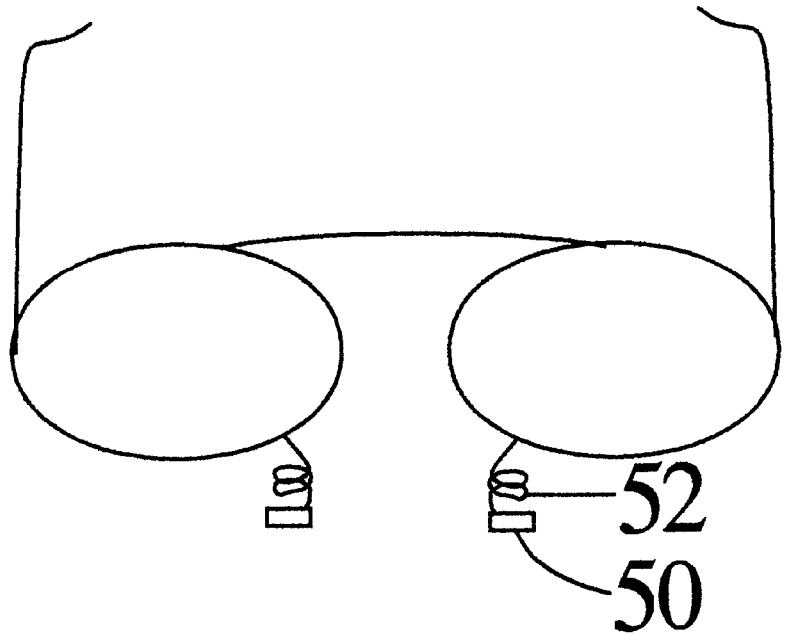
FIG. 5 shows a nasal dilator comprising a spring member having an end with an adhesive means.

FIG. 5 shows a nasal dilator configured with a spring member means(52) having a frame end and a nasal end, wherein the nasal end has an adhesive means(50) for adhering to nose. The spring member means may be attached to any portion of eyeglass frame structure, for example, the support bridges, nose pads, or lens receiving means.

Figure 4:
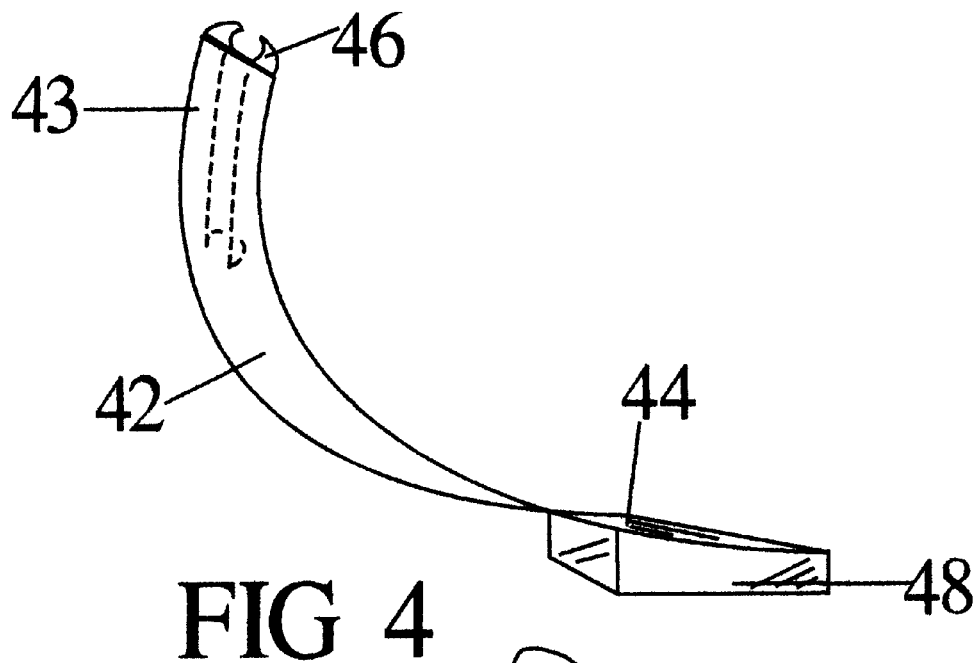
FIG. 4 is a view is an enlarged view showing a nasal dilator not in unity with eyeglasses and having a mechanical clip type engaging means.
Figure 4A:
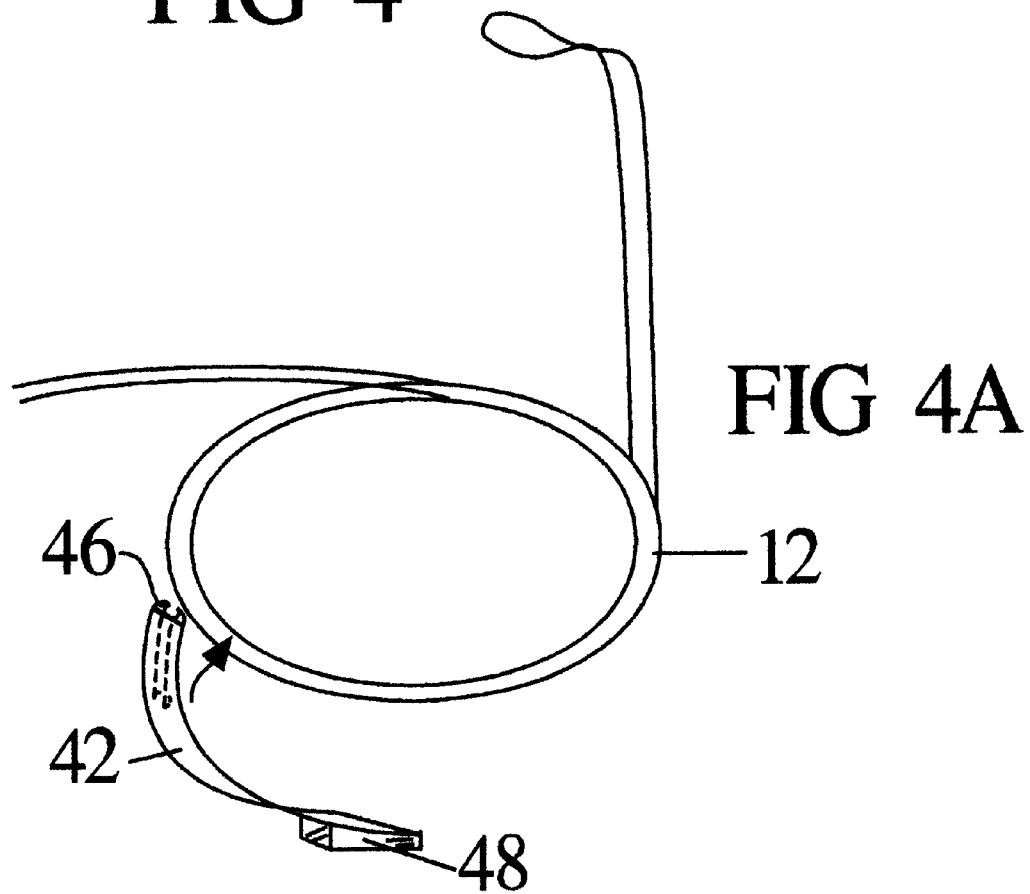
FIG. 4A is a view illustrating a nasal dilator means engaging the eyeglass frame member.
Figure 4B:
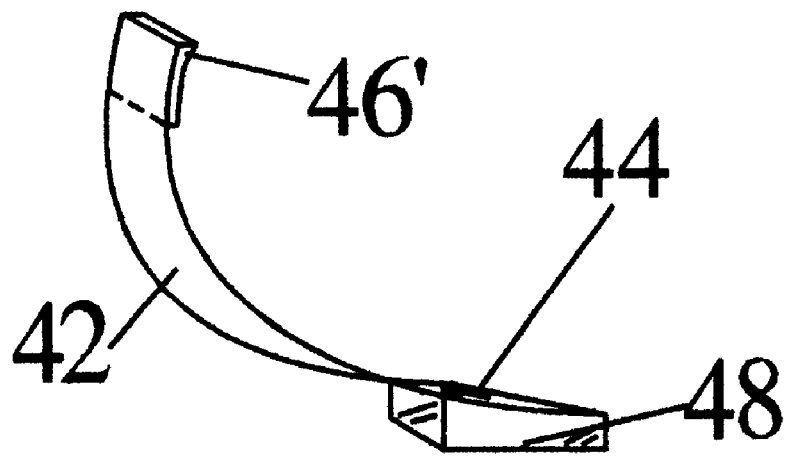
FIG. 4B is a nasal dilator having double sided adhesive means.
Figure 4C:
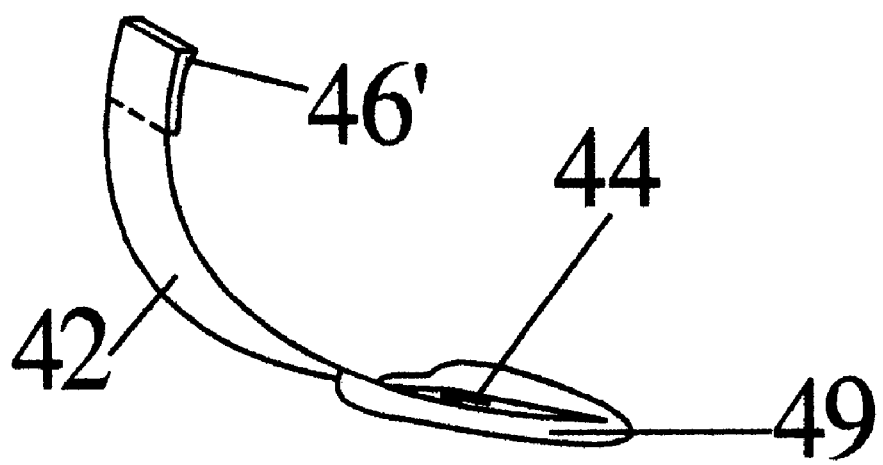
FIG. 4C is a nasal dilator having double sided adhesive means with the nasal end having an expanding adhesive means.
Figures 6, 6A:
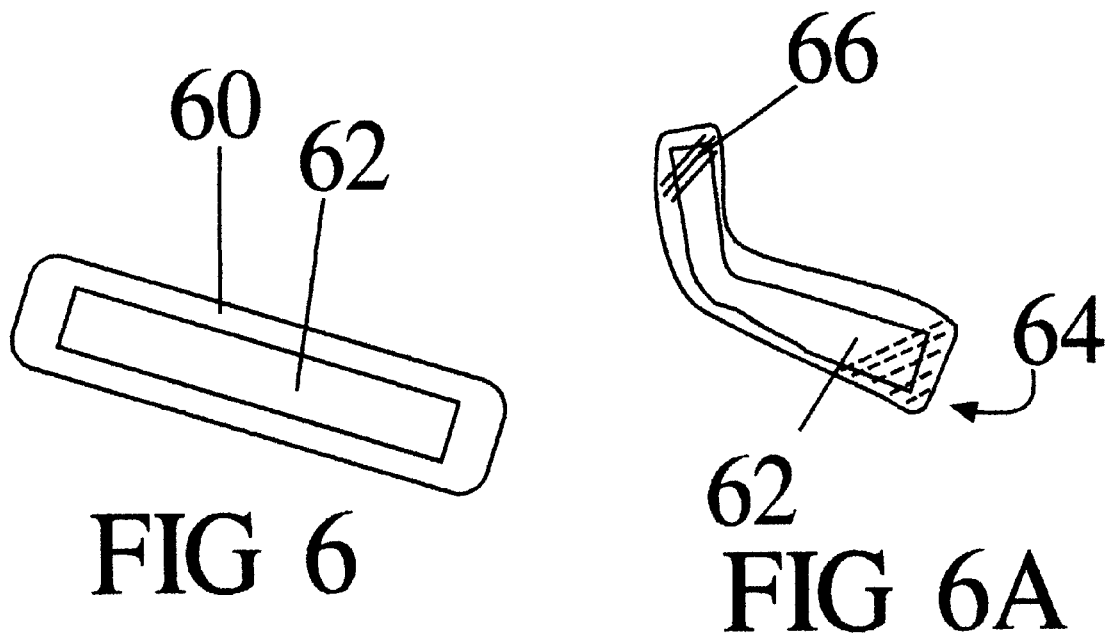
FIGS. 6, 6A show a nasal dilator comprising a truss with band and adhesive means.

An alternative embodiment are nasal dilators which are not unitary with an eyeglass frame structure, but which are used in conjunction with eyeglasses as seen in FIGS. 4–4C. FIG. 4B illustrates a device comprising a resilient band having a top, a bottom and two sides, each side comprising an adhesive means, one adhesive means placed near the top on the side facing the frame, and the other adhesive means placed near the bottom on the side facing the nose. FIG. 4C is a similar device as 4B with the band member surrounded by a truss adhesive(49). Thus, in this embodiment, the user places the top adhesive onto the eyeglass frame structure, e.g. nose pads, and the bottom adhesive onto the user's nose. In this embodiment, the user discards and replaces the nasal dilator. FIG. 4A and FIG. 4B shows the frame side of the resilient band member means comprising a mechanical engagement means, here exemplified by a clip means(46), for attaching to eyeglass frame member(12). The distal portion(44) of the resilient member means(42) comprises an adhesive means(48) for adhering the nasal dilator to a nose. FIG. 6 shows a nasal dilator having a truss(60) and resilient band(62). FIG. 6A shows truss in curvilinear shape having double sided adhesive means with a frame side adhesive(66) and a nasal side adhesive(64).

U.S. Pat. No. 5,533,503 is disclosed and is incorporated herein by reference. This patent teaches the anatomy of the nose and provides appropriate techniques and devices amenable to the practice of the instant invention.

Although the present invention has been described with reference to a preferred embodiment and with variation embodiments, individuals skilled in the art will recognize that changes may be made in form and detail without departing from the spirit and scope of the invention.

What I claim is:

1. An eyeglass frame structure having at lease one nasal dilator for preventing outer wall tissue of nasal passages of a nose from drawing in during breathing comprising:
    a frame member formed to define a pair of openings to receive lenses therein;
    a pair of temple members hingedly mounted to said frame member for holding said frame member onto a user's face;
    at least one nasal dilator means mounted onto said frame member for stabilizing the outside nasal tissue, thereby preventing drawing in during breathing;
    a means for attaching said nasal dilator means to said frame structure.

2. A device of claim 1 wherein said nasal dilator means comprises a spring member means for providing the potential energy to act to stabilize the outside nasal tissue.

3. A device of claim 2 wherein said spring member means comprises two ends, a nasal end and a frame end; and wherein said nasal end comprises a releasable adhesive means for releasably securing said nasal dilator means to a user's nose.

4. A device of claim 1 wherein said nasal dilator means comprises a resilient band member means for providing the potential energy to act to stabilize the outside nasal tissue.

5. A device of claim 4 wherein said resilient band member means comprises two sides, a nasal side and a frame member side; and wherein said nasal side comprises a releasably adhesive means for securing said nasal dilator to a user's nose.

6. A nasal dilator for use in conjunction with eyeglasses for preventing outer wall tissue of nasal passages of a nose from drawing in during breathing comprising:
    a spring member means having
        a first end region adapted to engage an eyeglass frame;
        a second end region adapted to engage the outer wall tissue of a nasal passage;
        an intermediate segment coupling the first end region to the second end region for acting to stabilize those outer wall tissues so engaged and thereby prevent such outer wall tissues of the nasal passages from drawing in during breathing.

7. A device of claim 6 wherein said second end region further comprises a releasable adhesive means for releasably securing said device to a user's nose.

8. A nasal dilator for use in conjunction with eyeglasses for preventing outer wall tissue of nasal passages of a nose from drawing in during breathing comprising:
    a resilient band member means having
        a first end region adapted to engage an eyeglass frame;
        a second end region adapted to engage the outer wall tissue of a nasal passage;
        an intermediate segment coupling the first end region to the second end region for acting to stabilize those outer wall tissues so engaged and thereby prevent such outer wall tissues of the nasal passages from drawing in during breathing.

9. A device of claim 8 wherein said second end region further comprises a releasable adhesive means for releasably securing said device to a user's nose.

10. A device of claim 8 wherein said resilient band member further comprises two sides, a frame side and a nasal side; wherein a releasable adhesive means is operatively attached to said frame side of the first end region for releasably securing the device to said eyeglasses.

11. A device of claim 10 wherein said resilient band member further comprises a releasable adhesive means operatively attached to said nasal side of the second end region for releasably securing the device to a user's nose.

12. A device of claim 8 wherein said first end region comprises a clip means for securing said nasal dilator to the eyeglasses.

13. A device of claim 8 wherein said resilient band member further comprises two sides, a frame side and a nasal side; wherein a releasable adhesive means is operatively attached to said frame side of the first end region for releasably securing the device to said eyeglasses and wherein a releasable adhesive means operatively attached to said nasal side of the second end region for releasably securing the device to a user's nose.

14. An eyeglass frame structure having at least one nasal dilator for preventing outer wall tissue of nasal passages of a nose from drawing in during breathing comprising:
 a frame member formed to define a pair of openings to receive lenses therein;
 a pair of temple members hingedly mounted to said frame member for holding said frame member onto a user's face;
 at least one nasal dilator means mounted onto said frame member for stabilizing the outside nasal tissue, thereby preventing drawing in during breathing;
 wherein said nasal dilator means comprises a spring member means for providing the potential energy to act to stabilize the outside nasal tissue; and wherein said spring member means comprises two ends, a nasal end and a frame end wherein said nasal end comprises a releaseabe adhesive means for releasably securing said nasal dilator means to a user's nose.

15. An eyeglass frame structure having a least one nasal dilator for preventing outer wall tissue of nasal passages of a nose from drawing in during breathing comprising:
 a frame member formed to define a pair of openings to receive lenses therein;
 a pair of temple members hingedly mounted to said frame member for holding said frame member onto a user's face;
 at least one nasal dilator means mounted onto said frame member for stabilizing the outside nasal tissue, thereby preventing drawing in during breathing; wherein said nasal dilator means comprises a resilient band member means for providing the potential energy to act to stabilize the outside nasal tissue; and wherein said resilient band member means comprises two sides, a nasal side and a frame member side wherein said nasal side comprises a releasably adhesive means for securing said nasal dilator to a user's nose.

16. A nasal dilator for use in conjunction with eyeglasses for preventing outer wall tissue of nasal passages of a nose from drawing in during breathing comprising:
 a resilient band member means having
  a first end region adapted to engage an eyeglass frame;
  a second end region adapted to engage the outer wall tissue of a nasal passage;
  an intermediate segment coupling the first end region to the second end region for acting to stabilize those outer wall tissues so engaged and thereby prevent such outer wall tissues of the nasal passages from drawing in during breathing;
  wherein said second end region further comprises a releasable adhesive means for releasably securing said device to a user's nose.

17. A device of claim 16 wherein said resilient band member further comprises two sides, a frame side and a nasal side; wherein a releasable adhesive means is operatively attached to said frame side of the first end region for releasably securing the device to said eyeglasses.

18. A device of claim 16 wherein said resilient band member further comprises a releasable adhesive means operatively attached to said nasal side of the second end region for releasably securing the device to a user's nose.

19. A device of claim 16 wherein said first end region comprises a clip means for securing said nasal dilator to the eyeglasses.

20. A device of claim 16 wherein said resilient band member further comprises two sides, a frame side and a nasal side; wherein a releasable adhesive means is operatively attached to said frame side of the first end region for releasably securing the device to said eyeglasses and wherein a releasable adhesive means operatively attached to said nasal side of the second end region for releasably securing the device to a user's nose.

21. A device of claim 1 wherein said nasal dilator is permanently attached to said eyeglass frame member.

22. A device of claim 1 wherein said nasal dilator is not permanently attached to said eyeglass frame member.

* * * * *